United States Patent
Gassel et al.

(10) Patent No.: US 12,221,647 B2
(45) Date of Patent: Feb. 11, 2025

(54) METHODS FOR ISOLATING MICROBIAL CELLS FROM A BLOOD SAMPLE

(71) Applicant: BACTERIA DETECTION LTD, Jerusalem (IL)

(72) Inventors: Aryeh Gassel, Jerusalem (IL); Yaron Suissa, Jerusalem (IL); Raphael Gassel, Jerusalem (IL); Maoz Tal, Moshav Aviezer (IL); Iaacov Man, Neve Yaakov (IL); Boaz Arieli, Mevaseret Tzion (IL)

(73) Assignee: BACTERIA DETECTION LTD, Jerusalem (IL)

( * ) Notice: Subject to any disclaimer, the term of this patent is extended or adjusted under 35 U.S.C. 154(b) by 0 days.

(21) Appl. No.: 17/526,048

(22) Filed: Nov. 15, 2021

(65) Prior Publication Data
US 2022/0064695 A1  Mar. 3, 2022

Related U.S. Application Data

(63) Continuation of application No. 15/759,217, filed as application No. PCT/IL2016/051006 on Sep. 11, 2016, now abandoned.

(60) Provisional application No. 62/217,093, filed on Sep. 11, 2015.

(51) Int. Cl.
*C12Q 1/24* (2006.01)
*C12N 1/00* (2006.01)
*C12Q 1/04* (2006.01)
*C12Q 1/6806* (2018.01)

(52) U.S. Cl.
CPC .............. *C12Q 1/24* (2013.01); *C12N 1/00* (2013.01); *C12Q 1/04* (2013.01); *C12Q 1/6806* (2013.01); *G01N 2800/26* (2013.01); *G01N 2800/44* (2013.01)

(58) Field of Classification Search
CPC .......... C12Q 1/24; C12Q 1/04; C12Q 1/6806; C12N 1/00; G01N 2800/26; G01N 2800/44; G01N 33/56911; G01N 33/56961; G01N 33/54326
See application file for complete search history.

(56) References Cited

U.S. PATENT DOCUMENTS

| 6,261,250 B1 * | 7/2001 | Phillips | A63B 21/4013 482/121 |
|---|---|---|---|
| 8,603,771 B2 * | 12/2013 | Stanley | C12Q 1/10 435/252.4 |
| 2002/0115077 A1 | 8/2002 | Einsele | |
| 2005/0014128 A1 * | 1/2005 | Ewert | C12Q 1/56 435/23 |
| 2011/0245483 A1 * | 10/2011 | Euting | C12N 15/1013 536/25.41 |
| 2012/0231446 A1 * | 9/2012 | Heckel | C12N 15/1003 536/25.4 |
| 2013/0171615 A1 * | 7/2013 | Van Meerbergen | C12Q 1/6806 435/6.15 |

FOREIGN PATENT DOCUMENTS

| EP | 2325312 | 5/2011 |
|---|---|---|
| WO | 9958644 | 11/1999 |
| WO | 2005089929 | 9/2005 |
| WO | 2009015484 | 2/2009 |
| WO | 2011070507 | 6/2011 |
| WO | 2011128086 | 10/2011 |
| WO | 2012001407 | 1/2012 |
| WO | 2012168003 | 12/2012 |
| WO | 2013091102 | 6/2013 |
| WO | 2013130759 | 9/2013 |
| WO | 2014082160 | 6/2014 |
| WO | 2016024263 | 2/2016 |

\* cited by examiner

*Primary Examiner* — David W Berke-Schlessel
*Assistant Examiner* — Susan E. Fernandez
(74) *Attorney, Agent, or Firm* — JMB Davis Ben-David

(57) ABSTRACT

This disclosure relates to methods for isolating bacterial cells, fungal cells, and single-celled parasites present in a blood sample containing higher eukaryotic cells; particularly wherein the microorganisms are present at a concentration significantly lower than the eukaryotic cells in the sample.

20 Claims, No Drawings
Specification includes a Sequence Listing.

METHODS FOR ISOLATING MICROBIAL CELLS FROM A BLOOD SAMPLE

CROSS REFERENCE TO RELATED APPLICATIONS

This is a Continuation of U.S. patent application Ser. No. 15/759,217, filed on Mar. 11, 2018, which is the US National Stage of International Patent Application No. PCT/IL2016/051006, filed on Sep. 11, 2016, which in turn claims priority to U.S. Provisional Patent Application No. 62/217,093, filed on Sep. 11, 2015. The contents of the foregoing patent applications are incorporated by reference herein in their entirety.

FIELD

Provided herein are methods for isolating microbial cells present in a blood sample containing higher eukaryotic cells; particularly wherein the microorganisms are present at a concentration significantly lower than the eukaryotic cells in the sample.

BACKGROUND

Bacteremia, Fungemia and, to a certain extent, Parasitemia, are conditions wherein a microbial pathogen penetrates the blood stream and is able to reproduce. Normally, the body can contain such infections but in some cases (i.e. weakened immune system), the pathogen is able to overcome and reproduce within the blood stream. This condition, if not properly treated can lead eventually to sepsis. Sepsis is a life-threatening illness in which inflammatory processes are triggered by the body in response to the constant/long lasting presence of infectious bacteria or other pathogens. The worldwide annual incidence of sepsis in 2013 was estimated to be 26 million cases.

For patients with symptoms of septic shock, current guidelines recommend the administration of antibiotics within one hour after diagnosis, whether it is a clinical, biochemical or molecular. However, in the absence of microbiological information within a short time frame, current practice relies on the empiric use of broad-spectrum antibiotics while the pathogen is cultured, identified and then subjected to antibiotic susceptibility testing over the course of several days.

Inadequate and/or delayed empirical antimicrobial therapy is a major cause of mortality, morbidity and increased hospital length of stay for sepsis patients. Mortality from sepsis increases at a rate of 8% for every hour that the patient is not receiving the correct antimicrobial therapy (Daniels, 2011). Approximately 30-50% of all patients presenting with the clinical symptoms of sepsis receive inappropriate antimicrobial therapy for the first several days, because the causative pathogen and its antibiotic resistance profile is unknown at the time therapy is initiated. The use of inappropriate antibiotics is also discouraged because it increases the burden of antibiotic resistance in general.

Many molecular methods exist for differential identification of bacterial and fungal DNA, RNA and proteins (e.g. by mass spectrometry (MS)). Methods for isolating microbial cells and/or DNA from a whole blood sample available at the time of initial presentation of sepsis symptoms would enable downstream use of these or similar molecular assays to provide data for patient treatment decisions in a clinically relevant and rapid time frame.

Methods have been developed for extracting DNA from intact microbial cells present in a non-blood sample and for purifying said microbial DNA so as to enable amplification by PCR. However none of the previously developed methods are sufficiently efficient to detect the potentially low concentration of a microorganism in the blood of a sepsis or pre-sepsis patient.

A common method comprises a first step of enzymatic lysis of the microbial cells, followed by extraction of the DNA, binding the extracted DNA to magnetic beads, immobilizing the beads with a magnet, washing away the non-DNA components in the sample, and eluting the now purified DNA from the beads into a PCR compatible buffer solution. However, such methods are not useful for blood samples containing small quantities of microbial pathogens and large amounts of non-microbial cellular material. For example, a 4 ml blood sample from a patient with sepsis may contain as few as 4 Colony Forming Units (CFU) of microbial cells, while also containing about $1.6 \times 10^7$ to $4.4 \times 10^8$ white blood cells (leukocytes) and about $6 \times 10^8$ to $1.6 \times 10^9$ platelets (thrombocytes). The high amount of non-microbial DNA if not properly addressed, can later compete with the limited microbial DNA during the subsequent DNA amplification. In addition, the large quantity of proteins, fats and other cellular components in the blood strongly decreases the efficiency of enzymatic lysis, PCR reactions and many other methods (e.g., fluorescence-mediated methods).

Accordingly, a continuing need exists for methods rapidly isolating microbial cells from whole blood for effective diagnosis of sepsis.

SUMMARY

Described herein are methods for isolating microbial cells from a blood sample containing or suspected of containing one or more microorganisms. The described methods include: providing an aqueous solution that includes a blood sample from a higher eukaryotic organism at any volume up to 5 ml or more than 5 ml in units of 5 milliliters in a test tube; and that contains at least reproducibly detected 5 CFU, with or without one anticoagulant agent or more; adding a first selective lysis reagent to the aqueous solution for a time period sufficient to lyse most of the higher eukaryotic erythrocytes and release hemoglobin from the erythrocytes, wherein the integrity of at least most microbial cells and higher eukaryotic leukocytes in the blood sample are preserved; separating and removing from the aqueous solution at least a portion of the higher eukaryotic proteins, including hemoglobin, while preserving most or all of the microbial cells; adding a second selective lysis reagent to the aqueous solution; incubating the aqueous solution for a time period sufficient to lyse higher eukaryotic leukocytes in the blood sample and release therefrom higher eukaryotic DNA, wherein the integrity of at least most microbial cells in the blood sample is preserved; introducing an endonuclease to the aqueous solution; incubating the aqueous solution for a time period sufficient to lyse higher eukaryotic DNA; adding to the aqueous solution an insoluble solid surface, and at least one of a water soluble polymer and an inorganic salt in a quantity sufficient to cause the blood plasma, the eukaryotic lysed blood cells' components and microorganisms to displace onto the solid surface; separating microbial cells mainly displaced onto the proteins coating the insoluble solid surface from the aqueous solution; eluting microbial cells from the proteins coating the solid surface by incubating the sample with a basic solution comprising protease;

and isolating released microbial cells from the solid surface and from at least a portion of the residual blood components in the solution.

The intact microbial cells isolated by the provided methods are then available for direct analysis or can be lysed and cellular components including DNA, RNA, and protein can be purified using known methods, for use in specific molecular detection of the microorganism.

The foregoing and other objects, features, and advantages will become more apparent from the following detailed description.

BRIEF DESCRIPTION OF THE DESCRIBED SEQUENCES

The nucleic and sequences provided herewith are shown using standard letter abbreviations for nucleotide bases as defined in 37 C.F.R. 1.822. Only one strand of each nucleic acid sequence is shown, but the complementary strand is understood as included by any reference to the displayed strand. The Sequence Listing is submitted as an ASCII text file named 2077_8_3001_SeqList.txt, created Nov. 15, 2021, about 1 KB, which is incorporated by reference herein. In the accompanying sequence listing:

SEQ ID NOs 1 and 2 are forward and reverse PCR primers for amplification of the MRSA (Methicillin-Resistant *Staphylococcus Aureus*) mecA gene.

SEQ ID NO 3 is a mecA probe oligonucleotide.

DETAILED DESCRIPTION

I. Terms and Definitions

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of this disclosure, suitable methods and materials are described below. The term "comprises" means "includes." Additionally, the terms "comprising" and "comprised of" are intended to include embodiments encompassed by the terms "consisting essentially of" and "consisting of." Similarly, the term "consisting essentially of" is intended to include embodiments encompassed by the term "consisting of." The abbreviation, "e.g." is derived from the Latin exempli gratia, and is used herein to indicate a non-limiting example. Thus, the abbreviation "e.g." is synonymous with the term "for example."

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

In case of conflict, the present specification, including explanations of terms, will control. In addition, all the materials, methods, and examples are illustrative and not intended to be limiting.

Amplification: When used in reference to a nucleic acid, any technique that increases the number of copies of the entire sequence of a nucleic acid molecule, or a portion thereof, in a sample or specimen. An example of amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid.

Aqueous sample: Any sample that is water-based. In particular embodiments, an aqueous sample or solution contains a blood sample mixed into it at 10%, 20%, 30%, 40%, 50% or even greater concentration. In other particular embodiments, the aqueous sample is a 100% blood sample that has been minimally processed, if at all, from the time of extraction from a subject to its provision for use in the described methods.

Bacteremia, Fungemia, Parasitemia (single cell): Conditions where a pathogen penetrates the bloodstream and is able to reproduce. This condition, if not properly treated, can lead to sepsis.

Blood sample: Any blood sample drawn from a subject. As used herein, a blood sample can be a 100% whole blood sample. In other embodiments, a blood sample can be diluted in a suitable aqueous solution to 90%, 80%, 70%, 60%, 50%, 40%, 30%, 20%, 10% or less of the starting sample concentration. A blood sample need not be whole blood, so long as a microbial-containing component of the original whole blood is retained. In particular examples, the blood sample is "substantially undiluted" such as those examples wherein the sample is collected in or transferred to a collection receptacle containing small quantities of a reagent such as heparin or citric acid, required for maintenance of the sample in liquid state and/or preservation of the blood sample. In other examples, a substantially undiluted blood sample contains no other reagents and, so as to maintain liquid state, is used in the described methods directly following collection from a subject.

Contacting: Placement in direct physical association. Includes both in solid and liquid form.

CFU: Colony Forming Unit: A unit used to estimate the number of viable microbial cells in a sample. Viable is defined as the ability to multiply via binary fission under controlled conditions.

Cycle Threshold (Ct): The cycle number in a real-time PCR reaction at which the slope of detected fluorescence passes a threshold. Used in the art for determining a positive indication of a detectable quantity of nucleic acid in a sample. In particular embodiments Ct can be used for comparing the relative quantity of nucleic acid in a series of samples amplified in parallel during a real-time PCR run. The lower the Ct value, the more nucleic acid is presumed to have been present in the sample.

DNA Purification: The separation of DNA from other cellular components. The process of DNA purification does not require 100% purity; however, the end-product of DNA purification is DNA that may be used in downstream applications such as DNA sequencing, PCR, real-time PCR and the like. In particular embodiments, DNA purification also serves to concentrate or enrich the DNA in a sample by preserving the quantity of DNA in a sample while reducing the quantity of fluid. In a particular embodiment, DNA purification involves binding DNA released and/or extracted from a cell to an uncoated magnetic surface, a specially coated magnetic surface, a silica surface, or a similar agent that binds DNA to an immobilized support; The surface in the preceding sentence may be in the form of a bead, a granule, a membrane, a hollow tube, a sieve or other types of surfaces. Washing away or otherwise removing other components of the sample that was with the DNA; and separating the isolated DNA with an elution buffer to separate the DNA from the support and draw it into a buffer solution in preparation for DNA amplification and/or identification, as for example, real-time PCR.

Detect: To determine if an agent (such as a signal or particular nucleotide nucleic acid probe) or a cell (such as a microbial cell) is present or absent. In some examples, this can further include quantification.

Determining expression of a nucleic acid: Detection of a level of expression in either a qualitative or a quantitative manner. In one example, it is the detection of nucleic acid sequence specific to a particular microbial pathogen. Similar procedures, such as PCR, can also be used to detect the quantity of DNA isolated from a sample.

Determining expression of a protein: Detection of a level of expression in either a qualitative or a quantitative manner. In one example, it is the detection of specific peptide sequence to a particular microbial pathogen. For example, Mass spectrometry can be used to detect the presence of proteins isolated from a sample.

Higher eukaryotic cell: A eukaryotic cell of a higher state of evolutionary development, such as those which occur for example in multicellular animal or plant organisms. In some embodiments, the higher eukaryotic tissue is from a mammal. In more specific embodiments, the higher eukaryotic tissue is from a human, and includes all non-microbial cells found within a human blood sample. In a particular embodiment, where the microbial cell is of a eukaryotic parasite or fungi, the term "Higher Eukaryotic Cell" refers to the host's cells.

Infectious disease: A disease caused by a pathogen, such as a fungus, parasite, bacterium or virus.

Isolated: An "isolated" biological component (such as a nucleic acid, protein, cell (or plurality of cells), tissue, or organelle) has been substantially separated or purified away from other biological components of the organism in which the component naturally occurs for example other tissues, cells, other chromosomal and extra-chromosomal DNA and RNA, proteins and organelles. Nucleic acids and proteins that have been "isolated" include nucleic acids and proteins purified by standard purification methods. Such isolated materials need not be 100% pure, but must be sufficiently pure from inhibitors of enzymes and other reagents used in downstream detection processes, such as PCR in the case of DNA.

Label: A detectable compound or composition that is conjugated directly or indirectly to another molecule to facilitate detection of that molecule. Specific, non-limiting examples of labels include radioactive isotopes, enzyme substrates, co-factors, ligands, chemiluminescent or fluorescent agents, haptens, and enzymes.

Lysis: The breaking down of a cell, often by chemical, temperature, enzymatic or mechanical mechanisms that compromise its integrity and allow for the extraction of DNA contained therein.

Microbe, Microbial cell, Microorganism: Refers to a diverse group of organisms, which exist in nature autonomously as a single cell or as a cell cluster, and therefore differ from higher eukaryotic cells (such as animal cells in a tissue, e.g. tissue cells of a mammal), that do not occur in nature as a single cell, but exclusively as macroscopic constituents of multicellular organisms. In some embodiments, microbial cells can be for example prokaryotic cells, such as bacteria or archaebacteria. In other embodiments microbial cells can be eukaryotic cells, such as yeasts, lower and higher fungi or protozoa.

As used herein, a prokaryotic cell or prokaryote can mean any cell or any organism belonging to the phylogenetic group of the Archaea or Bacteria (cf. Balows, Truper, Dworkin, Harder, Schleifer: *The Procaryotes* Chapter 142, pages 2696-2736 (1992)). Prokaryotic cells have clear differences from eukaryotic cells, which are reflected in structural characteristics of cellular organelles, a cell wall and the like. These characteristics are well known to a person skilled in the art, and also form the basis for distinctions between prokaryotic cell types. Thus, microbial cell or microorganism as used herein includes various genera of Gram-positive and Gram-negative bacteria, for example pathogenic bacteria of the genera *Enterococcus, Streptococcus, Staphylococcus, Salmonella, Legionella, Clamydia, Shigella, Pseudomonas, Listeria, Yersinia, Corynebacterium, Bordetella, Bacillus, Clostridium, Haemophilus, Helicobacter, Mycobacterium*, and *Vibrio*.

In other embodiments, the microbial cells or microorganisms can also include eukaryotic cells. Some embodiments of eukaryotic microbial cells are fungal cells. In more specific embodiments, the fungi include pathogenic fungi of the genera *Aspergillus* (e.g. *A. fumigatus, A. niger, A. flavus, A. nidulans*), *Basidiobolus* (e.g. *B. microsporus, B. ranarum*), *Cephalosporium* (e.g. *C. chrysogenum, C. coremioides, C. diospyri, C. gregatum*) and other pathogenic fungi of the genera *Entomophthora, Skopulariopsis, Mucor, Rhizomucor, Absidia, Rhizopus, Altenaria, Stemphylium, Botrytis, Chrysosporium, Curvularia, Helmithosporium, Hemispora, Nigrospora, Paecilomyces, Phoma, Thielavia* or *Syncephalastrum*. In other embodiments, pathogenic yeasts of the genus *Candida*, e.g. *C. albicans, C. guilliermondii, C. kruzei, C. parapsilosis, C. tropicalis* are also included.

Pathogen: A microorganism capable of causing a disease condition in a host, which is in some embodiments a human host and is in other embodiments a mammalian host, or in other embodiments an avian or vertebrate host.

Preserving the integrity: Indicates that the structural integrity of at least the majority of the microbial or pathogen cells is preserved to the degree that microbial DNA remains within the cells. A microbial cell whose integrity is preserved can also be referred to as an intact microbial cell. In certain embodiments, essentially all the microbial or pathogen cells in a sample remain intact.

Quantitative real time PCR: A method for detecting and measuring products generated during each cycle of a Polymerase Chain Reaction (PCR), which products are proportionate to the amount of template nucleic acid present prior to the start of PCR. The information obtained, such as an amplification curve, can be used to quantitate the initial amounts of template nucleic acid sequence.

Separation: Any process by which a mixture of one or more materials is separated into one or more distinct products or mixtures thereof. Particular examples of separation include filtration and density gradient centrifugation. In a particular example wherein the separation is filtration, the released components from cellular lysis are separated from cellular debris by passage through a filter having pores of a size sufficient to allow passage of the eluent while blocking passage of the cellular debris. In another example, cellular components are separated within a lysis mixture by fractionation using density gradient centrifugation. In yet another example, microbial cells bound to a solid surface are separated from the surrounding environment by removal of the solid surface from that environment.

Sepsis: A life-threatening illness in which inflammatory processes are triggered by the body in response to the presence of infectious bacteria or other pathogens. In particular embodiments, a subject can present to a medical professional with symptoms indicating a sepsis-related infection. However, in other embodiments, the infectious microorganism (bacteria or other pathogen) may be present in sufficiently low concentrations that symptoms have not developed. As understood herein, such a patient "has" sepsis.

Solid surface (or substrate): Any material which is insoluble, or can be made insoluble by a subsequent reaction. Numerous and varied solid surfaces are known to those in the art and include, without limitation, nitrocellulose, the walls of wells of a reaction tray, test tubes, polystyrene beads, ferro-magnetic beads, para-magnetic beads, magnetic beads, membranes, capillary tubes, sieves, granules, nanoparticles, ligand-coated particles, cross-linked particles, and microparticles (such as latex particles, silica, etc.). Except as otherwise physically constrained, a solid support may be used in any suitable shapes, such as beads, films, sheets, strips, or plates.

Under conditions sufficient for [carrying out a desired activity]: A phrase that is used to describe any environment that permits the desired activity.

II. Overview of Several Embodiments

Described herein are methods for isolating microbial cells from a blood sample containing or suspected of containing one or more microorganisms. The described methods include: providing an aqueous solution that includes a blood sample from a higher eukaryotic organism; adding a first selective lysis reagent to the aqueous solution for a time period sufficient to lyse most of the erythrocytes and release hemoglobin therefrom, wherein the integrity of at least most microbial cells and leukocytes in the blood sample are preserved; separating and removing from the aqueous solution at least a portion of the higher eukaryotic proteins, including hemoglobin, while preserving most or all of the microbial cells; adding a second selective lysis reagent to the aqueous solution; incubating the aqueous solution for a time period sufficient to lyse leukocytes in the blood sample and release therefrom higher eukaryotic DNA, wherein the integrity of at least most microbial cells in the blood sample is preserved; providing an endonuclease to the aqueous solution, and incubating the aqueous solution for a time period sufficient to lyse higher eukaryotic DNA; adding to the aqueous solution an insoluble solid surface, and at least one of a water soluble polymer and at least one inorganic salt in a quantity sufficient to cause blood plasma, blood cell components and microorganisms to displace directly or indirectly onto the solid surface; separating microbial cells displaced onto the solid surface from the aqueous solution; eluting microbial cells from the solid surface by incubating the sample with a solution that includes at least one protease; and isolating released microbial cells from the solid surface and from at least a portion of the residual blood components in the solution.

In particular embodiments, the aqueous solution includes at least one anticoagulant agent. In other embodiments the aqueous solution does not include an anticoagulant agent.

In some embodiments, the aqueous solution is a volume up to 5 ml, or is an up to 5 ml aliquot that is subdivided from an undiluted (100%) or diluted (5%-95%) larger blood sample volume.

In some embodiments, subsequent to adding the first lysis reagent to the aqueous solution, the aqueous solution is centrifuged for a time period sufficient to precipitate a majority of the microbial cells to facilitate removing at least a portion of the supernatant which includes higher eukaryotic proteins, such as hemoglobin, while preserving most or all of the microbial cells within the aqueous solution.

In further embodiments, subsequent to removing at least a portion of the supernatant from the aqueous solution and either (a) prior to adding to the aqueous solution a second lysis reagent, (b) in conjunction with adding to the aqueous solution a second lysis reagent, or (c) subsequent to adding to the aqueous solution a second lysis reagent, the method further includes adding an additional quantity of first lysis reagent to the aqueous solution, centrifuging the sample a second time and removing at least a portion of the supernatant from the aqueous solution while preserving most or all of the microbial cells within the aqueous solution.

In other embodiments, subsequent to adding to the aqueous solution a first lysis reagent, the aqueous solution is separated so as to cause at least a portion of the higher eukaryotic proteins, including hemoglobin, to be removed from the aqueous solution while most or all of the microbial cells are preserved in the aqueous solution.

In some embodiments, after adding to the aqueous solution the insoluble solid surface, the separated microbial cells are washed one or more times with a wash solution.

In particular embodiments, the microorganism is a bacterium, fungus, or single-celled parasite.

In some embodiments, the second selective lysis reagent comprises a non-ionic detergent. In other embodiments, the second selective lysis reagent also includes an agent capable of reducing viscosity, such as a deoxyribonuclease, and wherein incubating the aqueous solution containing said agent is a time period sufficient to reduce viscosity in the aqueous solution.

In some embodiments, the water soluble polymer is a dextran, PolyVinylPyrrolidone (PVP), or polyethylene glycol (PEG), which in particular examples can be added to a final concentration of 2%-20% w/v, inclusive.

In particular embodiments, the solid surface is magnetic, ferromagnetic or para-magnetic, and in those embodiments wherein separating the microbial cells comprises immobilizing the solid surface with a magnet, substantially all of the aqueous solution is removed.

In some embodiments, the wash solution includes at least one of a water soluble polymer and an inorganic salt, which in particular examples is at least one salt selected from the group consisting of: sodium chloride, magnesium chloride, calcium chloride, potassium chloride, lithium chloride, barium chloride, and cesium chloride.

In particular embodiments, the water soluble polymer in the wash solution is Dextran, PolyVinylPyrrolidone (PVP), or polyethylene glycol (PEG).

In some embodiments of the described methods, the protease is Proteinase K.

In further embodiments, the incubation in a protease is combined with, preceded and/or followed by agitation in a buffering solution at a pH above 8.

In additional embodiments, the ratio of the microbial cells to higher eukaryotic cells is at least 1:8000.

In other particular embodiments, the second selective lysis reagent is added simultaneous with, or prior to, the first selective lysis reagent.

III. Methods for Isolating Microbial Cells from a Blood Sample

Provided herein are methods for isolating microbial cells, such as bacterial, fungal or single parasite cells, present in a blood sample. The described methods enable early and accurate detection and identification of a pathogen in a subject suspected of or at risk of having a microbial infection.

The methods described herein are particularly useful for detecting low copy number of CFU and/or polynucleotides such as those of pathogens in higher eukaryotic cell-containing whole blood samples of subjects suspected to have sepsis preceded by bacteremia, parasitemia, or fungemia. Often in such samples, the volume of blood that can be drawn is limited, a large number of polynucleotide targets need to be queried, and the amount of non-pathogen DNA is much greater than the amount of pathogen DNA. In these circumstances, it is highly beneficial to remove the non-pathogen DNA and PCR (or alternative detection method) inhibiting substances prior to lysing the pathogen cells, while preserving a majority of the microbial cells, so as to minimize or eliminate competition during a subsequent microbial DNA purification process.

In a particular embodiment of the method, microbial cell isolation is performed by:

(A) Providing an aqueous solution comprising blood of a higher eukaryotic organism, optionally an anticoagulant agent, and also containing or suspected to contain a microorganism.

(B) Adding to the aqueous solution a first selective lysis reagent, incubating the aqueous solution for a time period sufficient to lyse at least most of the erythrocytes and extract hemoglobin therefrom, while preserving the integrity of microbial cells and leukocytes in the blood sample, and removing at least a portion of the aqueous solution containing hemoglobin and other higher eukaryotic proteins from that part of the aqueous solution containing the microbial cells and leukocytes, while preserving the integrity of at least most of the microbial cells.

(C) Incubating the aqueous solution containing the microbial cells and leukocytes in a second selective lysis reagent for a time period sufficiently long to lyse leukocytes in the sample, and extract higher eukaryotic DNA therefrom, while preserving the integrity of microbial cells that are in the solution.

(D) Adding to the aqueous solution containing the microbial cells and lysed leukocytes, a solid surface, a water soluble polymer and/or salt in a quantity sufficient to cause the blood plasma, the eukaryotic lysed blood cell components, and the microorganisms to displace onto the solid surface In this step, intact microbial cells present in the sample displace onto the solid surface either directly or indirectly through surface-bound proteins.

(E) Separating from the aqueous solution the solid surface as well as microbial cells and proteins bound directly thereto and intact microbial cells bound to the bound proteins.

(F) Adding an elution reagent comprising protease, eluting at least most of the intact microbial cells from the protein coated solid surface (e.g protein derived from various blood cells), and isolating released microbial cells from the solid surface and from at least a portion of the residual blood components in the solution.

In the described embodiment, Step B entails adding to an initial aqueous solution, such as a 100% blood solution or dilution thereof, a first selective lysis reagent sufficiently mild as to lyse erythrocytes, while preserving the integrity of at least most leukocytes and microbial cells in the blood solution. In particular embodiments, the first selective lysis reagent is water. In another embodiment, the water can be buffered with tris base, alone or in combination with Tris-EDTA (TE) so as to render the pH of the water from 7 to 9.5.

In the described embodiment, Step B further entails removing at least a portion of the higher eukaryotic proteins from the sample while preserving within the sample most or all of the microbial cells. This process can be achieved in a number of ways. In some embodiments, following incubation, the sample is centrifuged for sufficient time as to cause at least most of the microbial cells to precipitate to the bottom portion of the container and then at least a portion of the supernatant containing higher eukaryotic proteins is removed from the sample. In another embodiments, there is no distinct incubation period and, instead, the sample is incubated during centrifugation. In still other embodiments, instead of centrifugation, the sample is incubated and then separated from the supernatant by filtration, wherein at least most of the microbial cells are blocked from passage through the filter and at least a portion of the higher eukaryotic cellular components pass through the filter and are discarded.

In particular embodiments, the second selective lysis reagent includes a non-ionic detergent. In other embodiments, the second selective lysis reagent includes a non-ionic detergent and a deoxyribonuclease. It will be appreciated that the sequence with which the chemical components of the second selective reagent of Step C are added to the aqueous solution is not critical to the successful performance of the method. Accordingly, in some embodiments, a non-ionic detergent is added to the aqueous solution before adding an agent capable of reducing viscosity, such as deoxyribonuclease. In other embodiments, the viscosity reducing agent is added before a non-ionic detergent is added. In still other embodiments the reagent components of Step C (the "second selective lysis reagent") are added together with or even prior to the initial solution (the "first selective lysis reagent").

In particular embodiments, the solid surface may be a mesh, or a filter that permits aqueous solutions to pass through and yet contains solid surface onto which microbial cells can bind. In certain embodiments, the solid surface incorporates material that exhibits permanent magnetic behavior. In other embodiments, the solid surface is composed of material that exhibits magnetic behavior only when subjected to a magnetic field.

It is preferred that the solid surface has a high specific surface area and hence, preferably the solid surface is provided by beads. The term 'beads' includes, but is not limited to, insoluble magnetic particles that are spherical or irregular in nature and of size ranging from 0.1 micron to 10 micron in diameter. These include both (a) particles that are permanently magnetizable, being particles that exhibit bulk ferromagnetic properties, such as magnetic iron oxide or iron platinum, as well as (b) magnetically responsive particles, sometimes termed superparamagnetic particles, being particles that demonstrate magnetic behavior only when subjected to a magnetic field. In certain embodiments, the particles are nanoparticles that incorporate magnetic materials, or magnetic materials that have been functionalized, or may contain from 10% to 95% superparamagnetic particles or other configurations as are known in the art.

In particular embodiments, the solid surface is coated, as for example, carboxyl coated magnetic particles. In other embodiments, the solid surface is uncoated. A particular example of a solid surface or bead is uncoated magnetite particles that are highly susceptible to an external magnetic field. Production of magnetic particles is shown for example in Giaever (U.S. Pat. No. 3,970,518), Senyi et al. (U.S. Pat. No. 4,230,685), Dodin et al. (U.S. Pat. No. 4,677,055), Whitehead et al. (U.S. Pat. No. 4,695,393), Benjamin et al. (U.S. Pat. No. 5,695,946), Giaever (U.S. Pat. No. 4,018,886), Rembaum (U.S. Pat. No. 4,267,234), Molday (U.S. Pat. No. 4,452,773), Whitehead et al. (U.S. Pat. No. 4,554,088), Forrest (U.S. Pat. No. 4,659,678), Liberti et al. (U.S. Pat. No. 5,186,827), Own et al. (U.S. Pat. No. 4,795,698), and Liberti et al. (WO 91/02811), the content of each of which is incorporated by reference herein in its entirety.

According to some embodiments, microorganisms or microbial cells that are the subject of the invention include both prokaryotic microorganisms, such as Gram-positive bacteria and Gram-negative bacteria, and eukaryotic microorganisms, such as fungi.

Examples of prokaryotic microorganisms that can be isolated using the described methods include, but are not limited to pathogenic bacteria of the genera *Mycobacterium, Enterococcus, Streptococcus, Staphylococcus, Salmonella, Legionella, Clamydia, Shigella, Pseudomonas, Listeria, Yersinia, Corynebacterium, Bordetella, Bacillus, Clostridium, Haemophilus, Helicobacter* and *Vibrio.*

Examples of eukaryotic microorganisms that can be isolated using the described methods include, but are not limited to fungal and single parasitic cells. In more specific embodiments, the fungi include pathogenic fungi of the genera *Aspergillus* (e.g. *A. fumigatus, A. niger, A. flavus, A. nidulans*), *Basidiobolus* (e.g. *B. microsporus, B. ranarum*), *Cephalosporium* (e.g. *C. chrysogenum, C. coremioides, C. diospyri, C. gregatum*) and other pathogenic fungi of the genera *Entomophthora, Skopulariopsis, Mucor, Rhizomucor, Absidia, Rhizopus, Altenaria, Stemphylium, Botrytis, Chrysosporium, Curvularia, Helmithosporium, Hemispora, Nigrospora, Paecilomyces, Phoma, Thielavia* or *Syncephalastrum*. In other embodiments, pathogenic yeasts of the genus *Candida*, e.g. *C. albicans, C. guilliermondii, C. kruzei, C. parapsilosis, C. tropicalis* are also included. In another specific embodiment, the parasite include pathogenic *amoeba* (e.g. *Naegleria fowleri*) or *leishmania* (e.g. *Leishmania donovani*).

In other particular embodiments, particular microorganisms that can be isolated using the described methods include, are not limited to *Coagulase Negative Staphylococci, Staphylococcus aureus, Enterococcus* spp., *Candida* spp., *Escherichia coli, Klebsiella* spp., *Pseudomonas aeruginosa, Enterobacter* spp., *Serratia* spp., *Acinetobacter baumannii, Proteus* spp, *Streptococcus, Streptococcus pneumonia, Salmonella* and *Citrobacter.*

The sample for use herein is an aqueous solution that is entirely or in part a blood sample. The blood sample can be from a human or a non-human subject. In particular embodiments, the blood sample is 90%-100% blood extracted from the subject. In other embodiments, the blood sample is diluted to 1%-99% of the starting sample concentration, such as 98%, 95%, 90%, 80%, 70%, 60%, 50%, 40%, 30%, 20%, 10%, 5%, 2% or any dilution in between. The blood sample can be a whole blood sample; or it can be a fraction of a blood sample, so long as a microorganism-containing fraction of the blood sample is used.

As discussed further in Example 2, prior described methods of microorganism displacement onto solid surfaces are not operable in the context of a blood sample. In a particular embodiment, the blood sample is treated with one or more anticoagulant agents so as to prevent activity that will lead to calcification or particle aggregation at a later stage in the procedure, and then the blood sample must be pre-treated. Anticoagulant agents are well known and include, but not limited to EDTA, heparin and citric acid.

In addition, the described methods require that prior to adding a water soluble polymer and a solid surface to the blood sample, the blood solution must be pre-treated. First, the blood solution must be incubated in the presence of an added first selective lysis agent that (a) primarily lyses erythrocytes in the blood sample, (b) does not lyse most or all of the leukocytes in the blood sample and (c) does not lyse most or all of the microbial cells. Following the first stage, at least a portion of the hemoglobin and other higher eukaryotic proteins in the aqueous solution must be removed from the sample, thereby reducing the presence in the sample of blood components that inhibit subsequent microbial DNA isolation and amplification. Second, the blood solution must be incubated in agents that (a) lyse leukocytes in the sample, (b) do not lyse most or all of the microbial cells, and (c) do not interfere with later precipitation when an inorganic salt and/or a water soluble polymer are/is added to the blood sample.

Previous methods have been described for selectively lysing higher eukaryotic cells, such as cells in a blood sample, such as in an aqueous solution, while preserving the integrity of microbial cells present in the same solution. In the Molysis™ DNA isolation kit (Molzym) samples are incubated with chaotropic agents, such as guanidine, and DNase. In contrast, International Patent Publication WO 2011/070507 discloses the use of non-chaotopic non-ionic detergents together with an alkaline buffer rendering the solution with a pH of around 9.5 or higher.

In particular embodiments, higher eukaryotic cells, particularly leukocytes, in the blood sample are selectively lysed in Step C with a reagent containing chaotropic agents and/or non-ionic detergents. Non-ionic detergents include, but are not limited to Tween-20, Tween-40, Tween-60, Tween-80, Nonidet-P40, Deoxycholate, Brijj, Igepal, Triton, Octyl-beta-Glucoside, Digitonine, and Dodecyl-beta-D-maltoside. In other embodiments, the selective lysis reagent contains instead of a chaotropic agent, an alkaline buffer together with one or more non-ionic detergent.

Chaotropic agents, such as guanidine, denature substances released from higher eukaryotic cells which may increase viscosity of the solution, while incubation in alkaline buffers with a pH of 9.5 or higher and non-ionic detergents risks lysis of microbial cells in the solution. Accordingly, a preferred embodiment for selectively lysing higher eukaryotic cells comprises incubation in a solution containing one or more non-ionic detergent, and containing neither any chaotropic agent nor any alkaline buffer. In some embodiments, the non-ionic detergent is Tween-20 at a final concentration of between around 0.1% to 5%. In particular embodiments, the Tween-20 is at a final concentration of 0.1%, 1%, 2% or 3%.

Selective lysis of higher eukaryotic cells, including leukocytes (as shown in Step C of the above method), releases DNA into the aqueous solution, which increase viscosity and stickiness within the sample, making it more difficult to subsequently remove inhibitors of microbial lysis and other enzymatic reactions. In particular embodiments therefore, the described methods include the addition of an agent capable of degrading any DNA followed by incubating the aqueous solution for a time period sufficiently long so as to degrade the higher eukaryotic DNA, thereby reducing the viscosity and stickiness of the solution. Reduction in viscosity and stickiness makes it easier to mix the solution in order to remove residual blood material. Various deoxyribonuclease enzymes have been described and made commercially available. DNase 1 is one non-limiting example of such an agent for degrading DNA.

It is well known that the addition to an aqueous solution of PolyEthylene Glycol (PEG) and/or Sodium Chloride (NaCl) enhances the displacement of biological materials onto magnetic particles (U.S. Pat. No. 5,705,628; Saiyed et al. 2008). Such materials likewise can be used in the currently described methods. In certain embodiments, water soluble polymers such as PolyVinylPyrrolidone (PVP) or dextran can be used in place of PEG; and in other embodiments alternative inorganic salts can be used in place of sodium chloride, including, but not limited to, magnesium chloride, calcium chloride, potassium chloride, lithium chloride, barium chloride and cesium chloride.

By sharp contrast to the displacement of microbial cells onto solid surface magnetic beads in an aqueous solution containing a water soluble polymer and an inorganic salt, but not containing blood, described herein is the discovery that most of the microbial cells in an aqueous solution containing a solid surface (e.g. magnetic beads), a water soluble polymer, an inorganic salt, and blood tend not to bind directly to the surface of the magnetic beads. Instead, proteins present in the blood in much higher number/stoichiometry then the microorganism cells bind to the surface of the magnetic beads, coat the beads and the microbial cells tend to mainly bind to the magnetic bead-bound proteins, rather than directly to the beads.

It has been observed that a portion of the microbial cells detach during subsequent wash steps, even when a wash solution contains an identical concentration of PolyEthylene Glycol (PEG) and NaCl as the initial binding solution. It has also been observed that much of the detached microbial cells can be displaced to a solid surface and prevented from being discarded when wash solution is removed, by adding additional magnetic particles to the sample either together with the wash solution or prior to removal of the wash solution and incubating said sample with the magnetic particles for a period of time sufficient to facilitate binding of proteins in the sample to the new magnetic particles and binding of previously detached microbial cells to the bead-bound proteins.

The concentration of the water soluble polymer and/or salt added to the blood sample should be adjusted according to the nature of the polymer so as to produce the desired maximum displacement of the microbial cells from suspension in the blood onto the proteins coating the solid surface, such as magnetic particles. In particular embodiments, the final polymer concentration is from 8% to 15% (w/v), and preferably about 10% (w/v).

The water-soluble polymer can be a non-ionic hydrophilic polymer, for example a dextran, a PolyVinylPyrrolidone (PVP) or a PolyEthylene Glycol (PEG). The PEG can be polydisperse in molecular weight or monodisperse, branched or straight chain, and may be of a star type. The water soluble polymer can have an average molecular weight of from 200 or higher, such as from 1,000 to 20,000, and more preferably 5,000 to 13,000, (e.g. about 5,000; 6,000; 7,000; 8,000; 9,000; 10,000; 11,000; 12,000; or 13,000). These molecular weights are particularly suitable for PolyEthylene Glycol (PEG) or PolyVinylPyrrolidone (PVP).

In particular embodiments, a water-soluble inorganic salt either alone or in conjunction with a water soluble polymer, is used to raise the ionic strength of the aqueous liquid that includes or is a blood sample. The inorganic salt raises the ionic concentration of the liquid to a final concentration of 150 mM to 6M, and more preferably from 0.25 to 0.75M, e.g. 0.5M.

In a particular embodiment, to maximally displace microorganisms directly or through blood-proteins onto the solid surface while limiting displacement of impurities, contaminants and inhibitors from the blood, PEG is added to a final concentration between 9.5% and 10.5% (w/v), and sodium chloride is added to a final concentration between 0.5M and 0.75M.

As described herein, following displacement of the microorganism onto a protein coating a solid surface, such as onto metal particles, the particles can be immobilized, such as through use of a magnet. In particular embodiments, the particles are then washed at least one time with one or more wash solution.

The wash solution can include the same components as the displacement or binding solution. Accordingly in particular embodiments, the wash solution can contain the same final concentration of water soluble polymer and/or salt as in the binding solution. In other embodiments, the concentrations of polymer and/or salt in the wash solution are different than in the binding solution. In still further embodiments, the concentrations of polymer and/or salt in a first wash solution, may be different from the concentrations in a second, third or fourth wash solution. For example, a final concentration of 15% PEG and 1.5M sodium chloride, while less than optimal for the binding solution, may be appropriate for the solution used for one or more washes. In particular embodiments, the final polymer concentration is from 6% to 15% (w/v) alone and/or together a final concentration of between 150 mM of inorganic salt.

In still other embodiments, the wash solution can also contain additional magnetic particles, allowing proteins and microorganisms that become unbound during the wash process to displace onto a solid surface directly or microorganisms on top of said proteins.

Step F comprises eluting intact microbial cells from a protein coated solid surface, such as magnetic beads. In particular embodiments, this process is achieved by incubating the sample in an agent capable of degrading proteins. While not being bound to the theory, a possible explanation for the effectiveness of this process is that incubation in such an agent degrades the proteins within the sample that are bound in-between the magnetic particles and the microbial cells, thereby severing the bond and eluting the microbial cells.

Agents that may be used to degrade proteins include, but are not limited to at least one of Proteinase K, Brofasin, OB Protease, Qiagen Protease, Trypsin, and Pronase. In particular embodiments, Proteinase K is used to digest released eukaryotic proteins. Protocols for digestion of eukaryotic proteins using a solution containing Proteinase K are well known and include, but are not limited to, incubation for around 30 minutes at 37° C. and incubation for around 15 minutes at 60° C.

In a preferred embodiment, the process of incubating the sample in a protease solution is prefaced by adding to the sample an agent to raise the pH level of the solution, such as sodium hydroxide or tris base (for example, Trizma® base from Sigma-Aldridge) with a pH of higher than 8, such as between pH 8-11, such as approximately 8.5, 9, 9.5, 10, 10.5, and 11. In alternative embodiments, the buffering agent can be added to the sample together with the protease solution, immediately after the protease solution, both prior to and together with the protease solution or both prior to and subsequent to the protease solution. In still further embodiments, the sample is at least briefly agitated as part of the elution process.

Step F further comprises isolating released microbial cells from the solid surface and from at least a portion of the residual blood components in the solution. Isolation from the solid surface may be achieved in various ways. For a non-limiting example, magnetic force may be applied to hold the solid surface particles and degraded fragments of residual higher eukaryotic proteins bound to the solid surface particles, while the microbial cells together with the liquid in the solution are transferred to a separate tube or receptacle. In particular embodiments, the solution is then centrifuged for a sufficient time period as to precipitate the microbial cells at the bottom the receptacle, allowing supernatant containing additional residual blood components to also be removed from the sample and discarded.

The described methods provide isolated microbial cells for immediate assay, or microbial cell components, such as DNA, RNA, or protein, which may subsequently be extracted and purified in preparation for whole cell analysis or amplification and detection, as for example, by PCR. Methods for extracting, purifying and concentrating cellular components, such as DNA from isolated microbial cells are well known to those skilled in the art. For example, following removal of the solid surface particles, the solution may be incubated in a microbial lysis solution for a sufficient period of time so as to extract microbial DNA therefrom, the solution is then centrifuged for a sufficient time period as to precipitate residual blood components and supernatant containing microbial DNA is then isolated.

In a particular embodiment, the isolated microbial cells may be directly analyzed without the need for extraction and analysis of a cellular component. One example is the use of biosensors and high resolution optics.

IV. Methods for Isolating Microbial Cells from any Blood Sample Volume

The microbial cell isolation methods presented above are sufficiently sensitive so as to provide a minimum reproducible yield of at least 10 CFU from a starting sample that can be divided into up to 5 ml aliquots of the described starting aqueous solution containing blood. For example, a 7 ml blood sample from a subject can be divided into aliquots of 5 ml and 2 ml, both of which are then processed using the described methods of microbial cell isolation The following examples are provided to illustrate certain particular features and/or embodiments. These examples should not be construed to limit the disclosure to the particular features or embodiments described.

EXAMPLES

Example 1: Displacement of Bacteria onto Magnetite Beads in a Non-Blood Aqueous Solution An effective test for Bacteremia or Fungemia leading to sepsis requires the ability to detect a very low number of CFU. As few as two copies of pathogen cells or their DNA recovered from a whole blood sample (at volumes ranging from 150 ul and up to 5 ml or more). For this reason the efficiency of bacterial isolation in a sample must be maximized. This example shows how a combination of NaCl and PolyEthylene Glycol (PEG) can displace bacterial cells onto magnetite beads.

Method

To determine displacement, Methicillin-Resistant *Staphylococcus Aureus* (MRSA) bacteria were first incubated in polypropylene tubes at room temperature with and without magnetite beads, NaCl (final concentration 0.5M), and PEG (final concentration 10% w/v). Following the incubation, each sample tube was placed into a magnet, and a liquid portion of the sample separated from the beads was spread onto culture plates to determine the number of Colony Forming Units (CFU) remaining in the solution (i.e. that were not displaced onto beads, if present in the sample). Three bacterial culture plates were prepared from each sample and the colonies were counted after 48 hour incubation providing an average CFU count with a presumed 10% margin of error.

With this protocol, the following conditions were tested:
Sample 1: 10 ml solution: water, MRSA bacteria;
Sample 2: 20 ml solution: water, MRSA bacteria, 0.5 M NaCl, 10% PEG;
Sample 3: 20 ml solution: water, MRSA bacteria, magnetite beads, 0.5 M NaCl, 10% PEG.

To preserve consistency in bacterial concentration, double the volume was plated in Samples 2-3, as compared to Sample 1.

Results and Discussion

The mean result of the three bacterial culture plates for each sample is shown in Table 1.

TABLE 1

| CFU remaining after displacement | |
|---|---|
| Sample | % CFU of Control (#1) |
| 1-Control | 100% |
| 2-NaCl, PEG, No Beads | 85% |
| 3-Beads, NaCl, PEG | 10% |

As shown in Table 1, a comparison of Sample 2 to the Non-Displacement Control (Sample 1) suggests that, in the presence of displacement reagents without a magnetic solid surface, most of the bacterial cells remained viable and unbound. Comparing the results from Sample 3 to Sample 2 we see a significant improvement in displacement when PEG/NaCl is added to a non-blood solution, suggesting that the presence of a water soluble polymer and inorganic salt is significantly effecting displacement of intact bacterial cells to an insoluble magnetic solid surface.

Example 2: Attempting to Isolating Bacteria from Whole Blood without Pre-Treatment

Introduction

U.S. Pat. No. 8,603,771 (U.S. Pat. No. 8,603,771) and above Example 1 describe capturing onto a solid surface microorganisms present in an aqueous liquid by adding to the liquid a sufficient quantity of a water soluble polymer to displace said microorganisms from the liquid to the solid surface. U.S. Pat. No. 8,603,771 indicates that PEG is the preferred water soluble polymer for this purpose, and describes the method as a first step in isolating and purifying a microorganism to remove inhibitors to downstream assays such as PCR. U.S. Pat. No. 8,603,771 demonstrates the method using sputum or urine samples having a high concentration of microbial cells. However, the components of a blood sample are very different from sputum and urine, and U.S. Pat. No. 8,603,771 does not demonstrate its method in blood. Moreover, U.S. Pat. No. 8,603,771 does not demonstrate isolation of bacteria from even a simple aqueous solution in which a low concentration of micro-organisms is present in comparison to higher eukaryotic cells present in the solution, such as would be necessary for effective Bacteremia and Fungemia detection.

Method

To determine the utility of applying the method of U.S. Pat. No. 8,603,771 to microorganisms present in whole blood as compared to an aqueous solution not containing blood, an identical quantity of MRSA bacteria was added to a 10 ml sample of whole blood and into a 10 ml sample of purified water. The blood sample was human blood stored in an EDTA solution to prevent coagulation.

Both samples were incubated at room temperature for several minutes in binding solution (comprising a final concentration of 7% PEG, 0.5M NaCl and uncoated magnetite particles and 1% uncoated magnetite particles). The samples were then placed in a magnet (DynaMag-50 Dynal) to immobilize the magnetite particles, and the supernatant was removed and discarded. A wash solution (comprised of 10% PEG and 0.5M NaCl) was added to each sample. The samples were incubated, the magnetic particles immobilized and the liquid removed and discarded. The wash process was repeated two additional times.

When the blood sample was placed in a magnet to draw the magnetic particles from the solution to the tube edge, a gel-like deep red solution of blood material bound to the magnetic particles, moved with the particles to the magnetic edge, and separated from the less turbid supernatant. Repeated washes were unable to substantively separate the residual blood material from the magnetic particles or reduce the turbidity of the solution when removed from the magnet.

The samples were then subjected to a microbial lysis procedure consisting of incubation with a lysis solution (comprising 0.25% SDS and 50 mM NaOH) for 5 minutes at 96° C., followed by a return to room temperature and subsequent agitation for 5 minutes at 65° C. to elute DNA from the magnetic particles.

The samples were placed in a magnet to immobilize the magnetic beads. The supernatant from each sample was transferred to a separate Zymo-Spin™ Column and prepared for PCR using the reagents and protocol the Genomic DNA Clean & Concentrator Kit from Zymo Research. Duplicates from each sample were then assessed in real-time PCR using a primer-probe assay targeting the mecA gene present in the sample MRSA bacteria (using SEQ ID Nos. 1-3).

Results

MRSA microbial DNA was detected by PCR in both of the duplicates from the water solution. No PCR amplification was evident in either of the duplicates from the blood sample. Post microbial lysis, the blood samples continued to appear turbid with viscous gel-like residue from the blood remaining attached to the magnetic particles. While it can be assumed that the binding reagents succeeded in displacing microbial cells to the region of the magnetic solid support in the blood solution, they also appeared to have displaced particle aggregates of blood material that could not be washed away.

Discussion

As demonstrated herein, the method of U.S. Pat. No. 8,603,771 cannot effectively isolate bacteria from blood nor enable said bacteria to be purified. Instead, it was observed that in the context of a blood solution, the U.S. Pat. No. 8,603,771 method displaces to the solid surface higher eukaryotic cells, impurities, contaminants, and inhibitors from the blood, thereby eliminating the utility of the method for enabling isolation of microbial DNA as required for detecting DNA markers associated with sepsis in a patient.

Furthermore, it was also observed that without the pre-treatment described further herein, and in sharp contrast to other aqueous solutions, addition of magnetic particles and PEG to a blood sample produces particle aggregates and the solution assumes a gel-like viscosity, further eliminating any utility of the U.S. Pat. No. 8,603,771 method for sepsis detection. Taken together, the observations presented above demonstrate that not only is U.S. Pat. No. 8,603,771 insufficient for applications wherein the aqueous solution contains whole blood, but U.S. Pat. No. 8,603,771 is not applicable for detection of Bacteremia or Fungemia, leading to sepsis in a subject.

Example 3: Pre-Treatment of a Microorganism Containing Blood Solution with a First Selective Lysis Solution This example demonstrates the effects of pre-treatment of a blood and microbe containing solution prior to microbial cell displacement onto a magnetic surface. Sample pretreatment with an erythrocyte lysing solution was compared to pre-treatment with a non-lysing solution.

Method

To determine the effect on subsequent microbial cell displacement of pre-treatment, an aqueous solution containing whole blood and microorganisms was tested for the effects of an erythrocyte-lysing solution in contrast to a non-lysing solution. An identical quantity of MRSA bacteria was added to each of four 10 ml samples drawn from the same human whole blood sample, which had been stored in a citric acid solution to prevent coagulation. For a baseline control, an identical quantity of MRSA bacteria was transferred directly to a microbial culture plate, incubated for 48 hours and the cells counted.

Into the first two blood/MRSA samples were added the following erythrocyte-selective lysis solutions: 15 ml of water buffered with TE (pH=8.3) into sample 1, and 30 ml of water buffered with TE(pH=8.3) into sample 2.

The third and fourth samples served as non-lysis controls as follows: 10 ml of saline was added to sample 3 and 30 ml of saline was added to sample 4.

All four samples were centrifuged and the supernatant removed, leaving a concentrate of the sample. All four samples were then incubated for several minutes in 10 ml of binding solution (comprising a final concentration of 10% PEG, 0.5M NaCl and 1% uncoated magnetite particles). The samples were then placed in a magnet to immobilize the magnetite particles, and the liquid removed and saved. A wash solution (comprised of 10% PEG, 0.5M NaCl and 0.5% uncoated magnetite particles) was added to each sample. The samples were incubated, the magnetic particles immobilized and the liquid removed and saved. The wash process was repeated two additional times.

For each of the four samples, the liquids removed after the binding step and after each of the three washes were separately plated on a culture plate to determine the number of colony forming units remaining from each step (i.e. that were not displaced onto beads, if present in the sample). Three bacterial culture plates were prepared from each sample and the colonies were counted after 48 hours of incubation providing an average CFU count for each of the four samples. The CFU count from each of the four pre-treated samples was then compared to the average CFU count from the baseline control sample. For each sample, the difference between the CFU count from the baseline control sample that did not undergo any centrifugation or magnetic particle displacement and the CFU count from the sample that underwent centrifugation and displacement reflects the percentage of microbial cells in each sample that failed to displace or failed to remain displaced through the procedures.

Results and Discussion

The average percentage of MRSA CFU present in the bacterial culture plates for each step's sample as compared to the average percentage of MRSA CFUs present in the baseline control culture plates is shown in Table 2.

TABLE 2

Percentage of Microbial Sample Loss during Binding and Washing

| Sample | Pre-Treatment | Percentage |
| --- | --- | --- |
| 1 | 15 ml Selective Lysis | 26% |
| 2 | 30 ml Selective Lysis | 27% |
| 3 | 10 ml Saline | 78% |
| 4 | 30 ml Saline | 40% |

Pre-treating a 10 ml sample of whole blood containing microorganisms with saline effectively dilutes the sample and to some extent reduces viscosity, but does not lyse any of the cells within the sample. Even in the presence of a 3:1 dilution (30 ml of saline into 10 ml of blood) the results show a full 40% loss of microorganisms during subsequent binding and washes. The loss is even more substantial, reaching 78%, when the sample is diluted 1:1 (10 ml of saline into 10 ml of blood).

In contrast, the results demonstrate that pre-treating with a lysis solution selective for lysing human Red Blood Cells, such as TE buffered water, significantly enhances the effectiveness of subsequent centrifugation and binding the microbial cells to a solid support, reducing the microbial cell loss to under 28%, with no substantive difference evident between pre-treating with 15 ml or 30 ml of selective lysis.

Example 4: Protease Elution of Microbial Cells from Magnetic Particles in a Blood Solution Vs in a Non-Blood Aqueous Solution As shown above, in a non-blood aqueous solution containing solid surface magnetic particles, a water soluble polymer and inorganic salt, microbial cells displace directly onto solid surface magnetic particles. By contrast, we have discovered that in an aqueous solution comprising blood, solid surface magnetic particles, a water soluble polymer and an inorganic salt, proteins present in the blood displace onto the solid surface, substantially coating the magnetic particles and at least most of the microbial cells displace onto the magnetic particles bound proteins, rather than directly onto the particles. Furthermore, in a solution containing blood, subsequent incubation of the aqueous solution with a protease will degrade the proteins bound to the particles and enable the release of microbial cells, while no such elution is evident in a non-blood aqueous solution.

This difference between binding and elution in an aqueous solution containing blood and binding and elution in an aqueous solution containing no-blood is demonstrated in the following example.

Method

An identical quantity of MRSA bacteria was added to each of two 10 ml samples; 30% human blood in TE (pH=8.3) buffered water (Sample 1) and 100% TE (pH=8.3) buffered water (Sample 2). In addition, an identical quantity of MRSA bacteria was transferred directly to a microbial culture plate, incubated for 48 hours and the cells counted to serve as the baseline control.

A selective lysis solution (comprising molecular biology grade water, TE, Tween-20 and DNase 1) was added to each sample. The blood sample was then stirred at 37° C.

10 ml of binding solution (final concentration of 10% PEG-8000, 0.5M NaCl and 200 mg uncoated magnetite particles) was then added to each of Sample 1 and Sample 2. The samples were then stirred at 37° C. for a few minutes. The samples were then placed in a magnet to immobilize the magnetite particles (DynaMag-50 Dynal) while the supernatant of each was removed and discarded.

Proteinase K was then added to each sample and the solutions stirred for several minutes. Each sample was vortexed, then placed in a magnet to immobilize the magnetite particles and the liquid solution removed and saved.

200 μl from each sample was spread onto 3 culture plates to determine the number of colony forming units eluted from the magnetic particles and present in each solution. Three bacterial culture plates were prepared from each sample and the colonies were counted after 48 hours of incubation providing an average CFU count for each of the two samples. The average CFU count from each of the samples was then compared to the average CFU count from the baseline control sample. For each sample, the difference between the CFU count from the baseline control sample and the CFU count from the samples reflects the percentage of microbial cells that were displaced and subsequently eluted from the solid support magnetic particles.

Results and Discussion

The average percentage of MRSA CFUs present in the three bacterial culture plates for each sample as compared to the average percentage of MRSA CFUs present in the baseline control culture plates is shown in Table 3.

TABLE 3

Percentage of Microbial Cells Successfully Displaced and Subsequently Eluted

| Sample | | Percentage |
|---|---|---|
| 1 | 10 ml Human Whole Blood | 60% |
| 2 | 10 ml TE Buffered Water | 2% |

Incubation in a protease solution was able to elute a majority of the microbial cells off of the solid support when the initial sample contained blood. On the other hand, the protease solution had little effect on a sample that did not contain blood. In the presence of magnetic particles, PEG and NaCl in appropriate concentrations, microbial cells will directly bind to the magnetic particles in an aqueous solution that does not contain proteins. However, the results provide strong support for the conclusion that in a blood sample, where proteins are plentiful; at least a majority of the microbial cells will not bind directly to magnetic particles, but will instead bind to proteins that have coated the magnetic particles. Subsequently, when these bead-bound proteins are degraded, as for example when protease is then added to the solution, the bond holding the microbial cells is broken and the microbial cells detach from the protein coated magnetic particles.

Example 5: Effective Isolation of Microbial DNA from a Small Quantity of Whole Blood This example demonstrates positive performance of an embodiment of the described methods where the starting sample comprises less than 4 ml of blood.

Methods

Four blood samples were prepared, each comprising less than 5,000 CFU of MRSA bacteria and 3 ml of blood transferred from a larger human whole blood sample stored in citric acid.

Pre-Treatment: To each blood sample were added a First Lysis Solution (comprising 7 ml of molecular biology grade water and TE pH 8.3) and a Second Selective Lysis Solution (comprising Tween-20 and DNase 1 (Sigma Aldridge). The blood samples were then stirred for several minutes at 37° C.

Bead Binding: To each blood sample was then added 11 ml of biding solution (final concentration of 10% PEG-8000, 0.5M NaCl and 200 mg uncoated magnetite particles). The blood samples were then stirred at 37° C. for several minutes. The samples were then each placed in a magnet to immobilize the magnetite particles (DynaMag-50 Dynal) while the supernatant was removed and discarded.

Removal of Residual Blood Material: To each blood sample was added 20 ml of Wash Solution (comprising 10% PEG-8000, 0.5M NaCl and 100 mg uncoated magnetite particles) and the samples were stirred for 5 minutes. The blood samples were then placed in a magnet to immobilize the magnetite particles while the supernatant was removed and discarded. The wash process was repeated at room temperature a second and third time using the identical quantity of Wash Solution.

Elution: Each sample now consisting of microbial cells bound to protein coated magnetic particles. To each was added Tris Base, pH 10, the solution was vortexed and stirred for several minutes. Proteinase K was then added to each sample and the solution stirred for 5 minutes. Each sample was vortexed and then placed in a magnet to immobilize the magnetite particles while the supernatant containing the released intact microbial cells was transferred to a clean tube. The elution process was repeated a second time for each sample. The supernatant from the second elution for each sample was transferred to the same clean tube as the supernatant from the first elution and the solution centrifuged. In each sample, the released intact microbial cells precipitated to the bottom of the tube while the supernatant was removed and discarded. Each precipitant was then resuspended in saline (0.9% NaCl), centrifuged and the supernatant removed and discarded.

Microbial Lysis: For each sample, the precipitant was re-suspended in TE and heated to 96° C. to inactivate any residual enzymes. For each sample, Microbial Lysis Solution was added (comprising AchromoPeptidase). The tubes were incubated for several min at 37° C. in order to lyze the cells. Each lysed sample was then heated at 96° C. for a few minutes to inactivate the enzyme Preparation for PCR: Each sample containing the microbial DNA was centrifuged and the supernatant collected and added to a PCR Preparation Reagent tube comprising TE and $MgCl_2$.

A positive control sample was prepared with TE buffer and a comparable quantity of the same MRSA bacteria. DNA was extracted from the control sample using an enzymatic microbial lysis solution (comprising AchromoPeptidase, TE, and sucrose) and incubation at 37° C. followed by incubation at 96° C. The DNA solution was added into PCR Preparation Reagent tube comprising $MgCl_2$.

A negative control sample was prepared comprising TE.

All four blood samples were then assessed in duplicates, together with the positive control sample and negative control sample, in Real-Time PCR with a primer-probe assay targeting the MRSA mecA gene (using SEQ ID Nos. 1-3).

Results

The results are presented in Table 4.

TABLE 4

| | Sample | Cycle Threshold[1] | Delta Ct[2] |
|---|---|---|---|
| 1 | First Blood Sample | 26.26 | 0.65 |
| 2 | Second Blood Sample | 27.39 | 1.78 |
| 3 | Third Blood Sample | 26.24 | 0.63 |
| 4 | Fourth Blood Sample | 25.5 | −0.12 |
| 5 | Positive Control | 25.61 | |
| 6 | Negative Control | No Ct value | |
| 7 | Avg. of delta Ct | | 0.735 |

1. The Cycle Threshold (Ct) values for each of the four blood samples reflect an average of the duplicate PCR reactions run from each sample.
2. The Delta Ct value reflects the difference between the Ct values of the blood sample as compared to the Ct value of the Positive Control sample.

Discussion

The results demonstrate the effectiveness of the method. The differences in Ct value are within the range of normal variance for repeated samples, with an average Delta Ct of 0.735. The findings support the conclusion that, on average, at least 50% of the MRSA microbial cells present in the initial blood sample were retained throughout the procedure and present in the PCR reaction.

Example 6: Effective Isolation of Microbial DNA from 10 ml Whole Blood

This example demonstrates positive performance of a preferred embodiment of the described methods.

Methods

Two blood samples were prepared each comprising less than 5,000 CFU of MRSA bacteria plus 10 ml of human whole blood transferred from the same larger blood sample stored in EDTA.

First Pre-Treatment: To each blood sample was added 15 ml of the First Selective Lysis Solution (comprising molecular biology grade water and TE pH=8.3). The blood samples were then centrifuged, and supernatant was removed from each sample and discarded.

Second Pre-Treatment: To each sample was added a Second Selective Lysis Solution (comprising molecular biology grade water, TE pH=8.3, Tween-20 and DNase 1). The blood samples were then stirred at 37° C.

Bead Binding: To each blood sample was then added biding solution (final concentration of 10% PEG-8000, 0.5M NaCl and 200 mg uncoated magnetite particles). The blood samples were then stirred at 37° C. for several minutes. The samples were then each placed in a magnet to immobilize the magnetite particles (DynaMag-50 Dynal) while the supernatant was removed and discarded.

Removal of Residual Blood Material: To each blood sample was added Wash Solution (comprising 10 PEG-8000, 0.5 ml NaCl and uncoated magnetite particles) and the samples were stirred for 5 minutes. The blood samples were then placed in a magnet to immobilize the magnetite particles while the supernatant was removed and discarded. The wash process was repeated two additional times, using the identical quantity of Wash Solution.

Elution: Each sample now consisting of microbial cells bound to protein coated magnetic particles. To each was added tris base, the solution was vortexed and stirred. Proteinase K was then added to each sample and the solution stirred for 5 minutes. Each sample was vortexed and then placed in a magnet to immobilize the magnetite particles while the supernatant containing the released intact microbial cells was transferred to a clean tube. The elution process was repeated a second time for each sample. The supernatant from the second elution for each sample was transferred to the same clean tube as the supernatant from the first elution and the solution centrifuged. In each sample, the released intact microbial cells precipitated to the bottom of the tube while the supernatant was removed and discarded. Each precipitant was then resuspended in saline (0.9% NaCl), centrifuged and the supernatant removed and discarded.

Microbial Lysis: For each sample, the precipitant was resuspended in TE and heated to 96° C. for 5 minutes to inactivate any residual enzymes. For each sample, the solution was heated at 37° C. in Microbial Lysis Solution (comprising AchromoPeptidase, sucrose, and 50 mM NaOH,). Each lysed sample was then heated at 96° C., to inactivate the enzyme, and cooled.

Preparation for PCR: Each sample containing the microbial DNA was centrifuged and the supernatant collected into a PCR Preparation Reagent tube comprising $MgCl_2$.

A positive control sample was prepared with TE buffer and a comparable quantity of the same MRSA bacteria. DNA was extracted from the control sample using an enzymatic microbial lysis solution (comprising AchromoPeptidase, TE, and sucrose) and incubation at 37° C. followed by incubation at 96° C. The isolated MRSA DNA was then added to a PCR Preparation Reagent tube comprising $MgCl_2$.

A negative control sample was prepared comprising TE.

Both blood samples were then assessed in duplicates, together with the positive control sample and negative control sample, in Real-Time PCR with a primer-probe assay targeting the MRSA mecA gene (using SEQ ID Nos. 1-3).

Results

The results are presented in Table 4.

TABLE 4

| Sample | Cycle Threshold[1] | Delta Ct[2] |
|---|---|---|
| 1 First Blood Sample | 26.04 | 1.3 |
| 2 Second Blood Sample | 25.40 | 0.66 |
| 3 Positive Control | 24.74 | |
| 4 Negative Control | No Ct value | |
| 5 Avg. of delta Ct | | 0.98 |

1. The Cycle Threshold (Ct) values for each of the blood samples reflect an average of the duplicate PCR reactions run from each sample.
2. The Delta Ct value reflects the difference between the Ct values of the blood sample as compared to the Ct value of the Positive Control sample.

Discussion

Positive results were evident for both the blood samples and the positive control sample. The absence of amplification in the negative samples indicates that the experiment was free of DNA contamination. The differences in Ct value are within the range of normal variance for repeated samples, with an average Delta Ct of less than 1 Ct.

These findings demonstrate the efficiency of an embodiment of the described method to provide at least 50% microbial DNA from a starting sample consisting of microbial pathogen in 10 ml of whole human blood.

Example 7: Effective Identification of a Microbe of Low CFU Titer in Whole Blood The previous examples illustrate isolation of microbial cells and/or DNA in a whole blood solution. This example demonstrates identification of a microbe in a processed blood sample in which the microbe is present in low titers similar to that which might be present in an early infection.

Approximately 100 CFU of a microbe (as specified in table 5 below) were added to a 4 mL blood sample with citrate. Microbial cells were then isolated in the following way: In each sample, TE buffered water was added to the samples. Tween 20 and DNAse were then added and the samples incubated 5 min at 37° C., to lyse the leukocytes without breaking the microbial cells and to eliminate higher eucaryotic DNA. The samples were then centrifuged, most of the supernatant was removed. Binding solution was added to the sample (final concentration of 10% PEG, 0.5M NaCl and 100 mg of uncoated magnetite), then incubated, with shaking, at 37° C. The sample tubes were then placed in a magnet to immobilize the magnetite particles (DynaMag-50 Dynal) while the supernatant was removed and discarded. The microbes were eluted by incubation, with agitation, at 37° C., in the presence of Tris-base solution, and Proteinase K. The sample tubes were then placed in a magnet to immobilize the magnetite particles while the supernatant was removed to new tubes and cleaned with Saline. The samples were resuspended in saline, CFU isolated from the samples were determined by plating and incubating the plates. The results are presented in Table 5.

TABLE 5

| | Sample | Total CFU in sample | % of control |
|---|---|---|---|
| 1 | Staphylococcus aureus MRSA ATCC BAA-40 | 137 | 39% |
| 2 | Candida albicans ATCC 10231 | 90 | 25% |
| 3 | Pseudomonas aeruginosa ATCC 13437 | 87 | 79% |

Discussion

In this example, low amount of microbes in the presence of 4 ml blood were purified. The process eliminated most of the blood content and eukaryotic DNA, while the bacteria remained viable. The efficiency of microbial elution was between 25%-79% of the initial bacterial spike. Thus, the above described methods not only are able to isolate viable microbial cells added to the blood sample, but also enable the use of molecular detection based methods which are sensitive and allow minute amounts of microbe detection. Other prior options cannot use these molecular methods since they either fail to recover the microbes at sufficient efficiency, and/or fail to clean and separate the blood from the microorganisms.

REFERENCES

Daniels, R, Journal of Antimicrobial Chemotherapy, 2011, 66 (suppl 2): ii11-ii23.
Saiyed, Z. M. et al 2008, Journal of Physics; Condensed Matter, 20: 204153, 1-5.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

---

We claim:

1. A method for isolating bacterial cells from a blood sample containing or suspected of containing one or more bacteria, the method comprising:
   providing a blood sample from a mammal;
   adding a first selective lysis reagent and a second selective lysis reagent comprising a non-ionic detergent to the blood sample and incubating the blood sample for a time period sufficient to lyse most of the erythrocytes and release hemoglobin therefrom, and for the non-ionic detergent to lyse leukocytes in the blood sample and release mammalian DNA therefrom, wherein most bacterial cells in the blood sample are preserved;
   separating and removing from the blood sample at least a portion of the mammalian proteins, including hemoglobin, while preserving most or all of the bacterial cells;
   incubating the sample with an endonuclease, for a time period sufficient to lyse mammalian DNA;
   adding an insoluble solid surface, and at least one of a water soluble polymer and at least one inorganic salt in a quantity sufficient to cause blood plasma, blood cell components and bacteria to displace directly or indirectly onto the solid surface;
   separating bacterial cells displaced onto the solid surface;
   eluting bacterial cells from the solid surface by incubating the bacterial cells on the solid surface with a solution comprising at least one protease; and
   isolating released bacterial cells from the solid surface.

2. The method of claim 1, wherein at least one anticoagulant agent is added to the blood sample prior to the first and second selective lysis reagents.

3. The method of claim 1, wherein the provided blood sample is a 5 ml undiluted sample or a 5 ml diluted sample that comprises 5%- 95% of an undiluted larger sample.

4. The method of claim 1, wherein, subsequent to adding the first and second lysis reagents, the blood sample is centrifuged for a time period sufficient to precipitate a majority of the bacterial cells to facilitate removing at least a portion of the supernatant comprising mammalian proteins, including hemoglobin, while preserving most or all of the bacterial cells within the sample.

5. The method of claim 1, wherein, subsequent to adding the first and second lysis reagents to the blood sample, the blood sample is separated so as to cause at least a portion of the mammalian proteins, including hemoglobin, to be removed from the solution while most or all of the bacterial cells are preserved in the solution.

6. The method of claim 1, wherein subsequent to adding the insoluble solid surface, the separated bacterial cells are washed one or more times with a wash solution.

7. The method of claim 6, wherein the wash solution comprises a water soluble polymer and an inorganic salt.

8. The method of claim 7, wherein the inorganic salt in the wash solution is at least one salt selected from the group consisting of: sodium chloride, magnesium chloride, calcium chloride, potassium chloride, lithium chloride, barium chloride, and cesium chloride.

9. The method of claim 8, wherein the water soluble polymer in the wash solution is, polyvinylpyrrolidone (PVP), or polyethylene glycol (PEG).

10. The method of claim 1, wherein the second selective lysis reagent further comprises an agent capable of reducing viscosity, and wherein incubating the blood sample with the first and second lysis reagents comprises a time period sufficient to reduce viscosity in the blood sample.

11. The method of claim 10, wherein the agent capable of reducing viscosity is a deoxyribonuclease.

12. The method of claim 1, wherein the at least one water soluble polymer is a dextran, polyvinylpyrrolidone (PVP), or polyethylene glycol (PEG).

13. The method of claim 12, wherein the final concentration of PEG is 2%-20% w/v.

14. The method of claim 1, wherein the solid surface is magnetic, ferromagnetic or para-magnetic, and wherein separating the bacterial cells comprises immobilizing the solid surface with a magnet, thereby removing the solution.

15. The method of claim 1, wherein the at least one protease is Proteinase K.

16. The method of claim 1, wherein incubation in the at least one protease is combined with, preceded and/or followed by agitation in a buffering solution at a pH above 8.

17. The method of claim 1, wherein the ratio of the bacterial cells to mammalian cells is at least 1:8000.

18. A method for isolating fungal cells from a blood sample containing or suspected of containing one or more fungi, the method comprising:
   providing a blood sample from a mammal;
   adding a first selective lysis reagent and a second selective lysis reagent comprising a non-ionic detergent to the blood sample and incubating the blood sample for a time period sufficient to lyse most of the erythrocytes and release hemoglobin therefrom, and for the non-ionic detergent to lyse leukocytes in the blood sample and release mammalian DNA therefrom, wherein at least most of the fungal cells in the blood sample are preserved;
   separating and removing from the blood sample at least a portion of the mammalian proteins, including hemoglobin, while preserving most or all of the fungal cells;
   incubating the sample with an endonuclease, for a time period sufficient to lyse mammalian DNA;
   adding an insoluble solid surface, and at least one of a water soluble polymer and at least one inorganic salt in a quantity sufficient to cause blood plasma, blood cell components and fungi to displace directly or indirectly onto the solid surface;
   separating fungal cells displaced onto the solid surface;
   eluting fungal cells from the solid surface by incubating the fungal cells on the solid surface with a solution comprising at least one protease; and
   isolating released fungal cells from the solid surface.

19. The method of claim 18, wherein subsequent to adding the insoluble solid surface, the separated fungal cells are washed one or more times with a wash solution comprising a water soluble polymer and an inorganic salt.

20. A method for isolating bacterial cells from a blood sample containing or suspected of containing one or more bacteria, the method comprising:
   providing a blood sample from a mammal;
   adding a first selective lysis reagent and a second selective lysis reagent comprising a non-ionic detergent to the blood sample and incubating the blood sample for a time period sufficient to lyse most of the erythrocytes and release hemoglobin therefrom, and for the non-ionic detergent to lyse leukocytes in the blood sample and release mammalian DNA therefrom, wherein most bacterial cells in the blood sample are preserved;
   separating and removing from the blood sample at least a portion of the mammalian proteins, including hemoglobin, while preserving most or all of the bacterial cells;

incubating the sample with an endonuclease, for a time period sufficient to lyse mammalian DNA;

adding an insoluble solid surface, and at least one of a water soluble polymer and at least one inorganic salt in a quantity sufficient to cause blood plasma, blood cell components and bacteria to displace directly or indirectly onto the solid surface;

separating bacterial cells displaced onto the solid surface;

eluting bacterial cells from the solid surface by incubating the bacterial cells on the solid surface with a solution comprising at least one protease; and isolating released bacterial cells from the solid surface, wherein the bacterial cells isolated are methicillin-resistant *Staphylococcus aureus* (MRSA).

* * * * *

SEQUENCE LISTING

```
<160> NUMBER OF SEQ ID NOS: 3

<210> SEQ ID NO 1
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 1
tgattatcca ttttataatg ctcaaatttc                                      30

<210> SEQ ID NO 2
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 2
gctatagatt gaaaggatct gtactgg                                         27

<210> SEQ ID NO 3
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 3
ccaggcacct tgtccgtaac ctgg                                            24
```